United States Patent [19]

Millet

[11] 4,249,530
[45] Feb. 10, 1981

[54] HYPODERMIC SYRINGE ASSEMBLY

[75] Inventor: Marcus J. Millet, New York, N.Y.

[73] Assignee: Johnson & Johnson, New Brunswick, N.J.

[21] Appl. No.: 37,584

[22] Filed: May 9, 1979

Related U.S. Application Data

[63] Continuation of Ser. No. 836,109, Sep. 23, 1972, abandoned.

[51] Int. Cl.³ .............................................. A61M 5/00
[52] U.S. Cl. ................................ 128/218 N; 128/221
[58] Field of Search .............. 128/218 N, 218 R, 221, 128/215, 216

[56] References Cited

U.S. PATENT DOCUMENTS

| 4,040,421 | 8/1977 | Young | 128/218 N |
| 4,121,588 | 10/1978 | Geiger | 128/218 N X |

Primary Examiner—John D. Yasko
Attorney, Agent, or Firm—Donal B. Tobin

[57] ABSTRACT

A hypodermic syringe assembly comprises a barrel with an axial bore, a hollow tip integral with the barrel having an internal surface defining a passageway communicating with the axial bore and also having a tapered external surface adapted to mate with the female tapered surface of a conventional needle hub, a needle hub having a bore therethrough removably positioned in and occupying substantially the entire volume of the passageway and a hollow needle secured within the bore of the hub in fluid communication with the axial bore of the barrel. The syringe assembly may be used with the unique hub positioned within the passageway to provide a substantially air-free syringe or the hub and needle may be removed from the tip to permit a conventional needle hub to be placed thereon.

2 Claims, 4 Drawing Figures

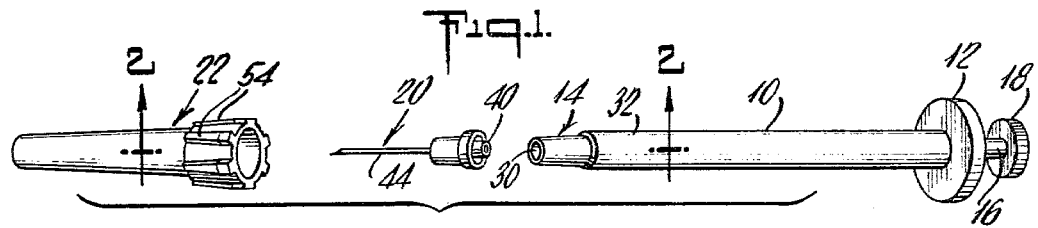
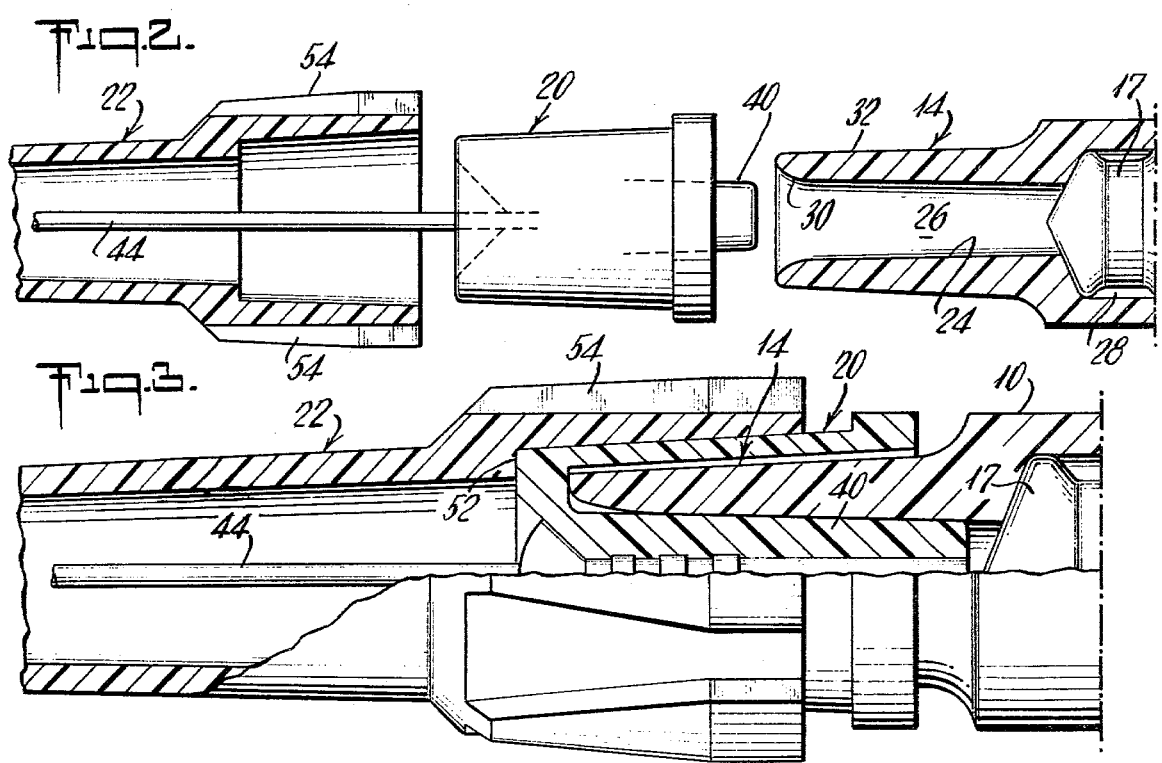
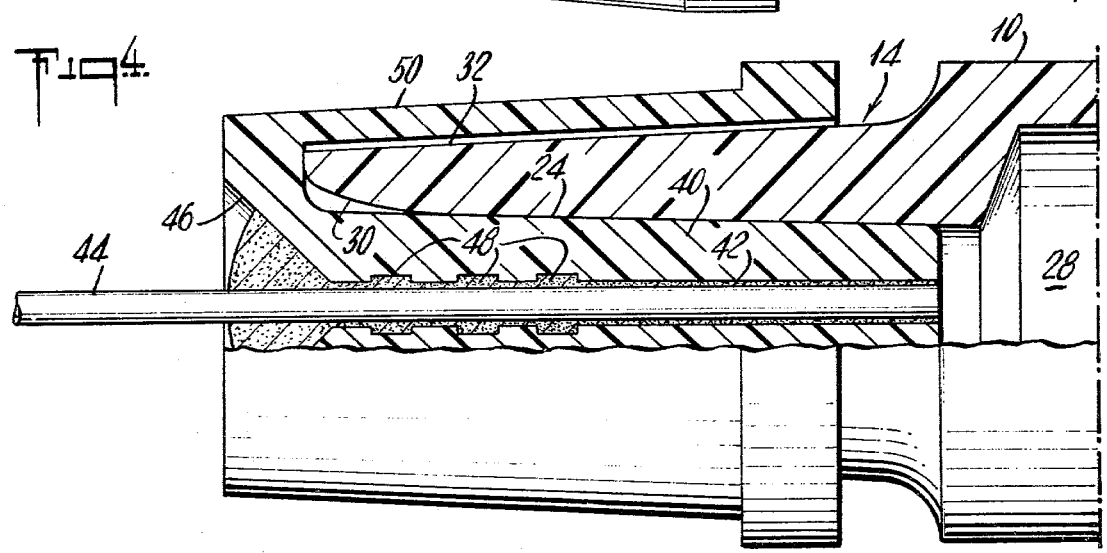

HYPODERMIC SYRINGE ASSEMBLY

This is a continuation of application Ser. No. 836,109, filed Sept. 23, 1977 now abandoned.

BACKGROUND OF THE INVENTION

This invention relates to a hypodermic syringe assembly and, more particulary, to a unique syringe assembly that may be utilized as a substantially air-free syringe or as a conventional syringe.

Presently, syringes that are constructed to be used with removable, interchangeable needles suffer from the presence of a large dead air space in the distal end of the assembly. This results in the presence of a substantial air bubble when medication is drawn into the syringe, which leads to the inconvenience of purging the air bubble from the syringe before making the injection. Although several different constructions have been proposed and used for making a syringe with a reduced air bubble, it has heretofore been impossible to provide a syringe assembly which has a reduced air bubble as assembled by the manufacturer but which can be disassembled and used as a conventional needle at the option of the user.

One such prior construction which provides an essentially air-free configuration is illustrated and described in U.S. Pat. No. 3,380,450, which issued on Apr. 30, 1968 to W. H. Adelberger. This patent describes a syringe assembly utilizing a needle hub which is positioned within the bore of a projection extending from the syringe barrel. By thus positioning the needle hub, the bore of the projection is substantially filled with the hub and reduces the volume which is normally present with a conventional needle hub arrangement.

Although the needle hub of the Adelberger patent may be removed from the syringe projection by rupturing a seal that is formed during the manufacturing process, the remaining syringe barrel and projection would be rendered useless by this act in that it would thereafter be incapable, as illustrted and described, of accommodating a conventional needle hub and, therefore, the syringe is actually designed to perform only a single function. In addition to the Adelberger device, other attempts have been made to provide syringe assemblies that may be utilized without the necessity of purging the air therefrom prior to use. However, none of the known prior devices have provided such an assembly that can also be utilized, if desired by the user, with a conventional needle hub.

SUMMARY OF THE INVENTION

The present invention provides a hypodermic syringe assembly that, at the option of the user, may be utilized in its manufactured form as an essentially air-free syringe or it may be utilized with a conventional needle/-hub assembly by merely removing the needle hub provided during the manufacturing operation.

This is accomplished by providing a syringe barrel which has an axial bore extending therethrough and a hollow tip integral with one end thereof. The tip is provided with an internal surface which defines a passageway situated to communicate with the axial bore of the syringe barrel. A uniquely designed hub having a bore therethrough is removably positioned in and occupies substantially the entire volume of the tip passageway. The passageway and the hub preferably have mating tapers to facilitate fabrication and utilization of the device. A hollow needle is secured within the bore of the hub in fluid communication with the axial bore of the syringe barrel and the hub is further provided with a skirt member that extends from its distal end to cover the external surface of the hollow syringe tip.

As used herein, the word "proximal" shall mean that portion of an element which, during normal use, would be at a location nearest the operator. For example, during the insertion of a syringe needle into a patient's arm, the thumb-contacting button of the syringe plunger would be at the proximal end of the syringe. Whereas, the needle point of the syringe would be at a location remote from the proximal end and this end shall be defined in this specification as the "distal" end.

The primary improvement of the present invention is the utilization of a taper on the external surface of the syringe tip in combination with the uniquely designed needle hub. This tapered external surface of the syringe tip is adapted to mate with the female tapered surface of a conventional needle hub. By thus fabricating the hypodermic syringe assembly, the assembly may be used, as manufactured, with the unique hub positioned within the tip passageway to provide a substantially air-free syringe or the hub and the needle may be removed from the tip to permit a conventional needle hub to be placed thereon.

Preferably, the taper provided on the syringe tip is a luer taper. This is preferred, because a "luer" taper is a conventional taper that has become a standard in the medical device field. Essentially all medical devices, such as, syringes, catheters, etc., have luer tapered connectors in order to achieve uniformity and avoid complication during use of the devices by the medical profession.

Thus, the present invention provides a dual-function hypodermic syringe assembly that has heretofore been unavailable.

BRIEF DESCRIPTION OF THE DRAWING

The invention will be particularly described with reference to the following detailed description of the preferred embodiment of the invention when considered together with the attached drawing, in which:

FIG. 1 is an assembly drawing illustrating the individual components of the unique hypodermic syringe assembly of the present invention;

FIG. 2 is a partial cross sectional view illustrating the alignment of the various components of the syringe assembly prior to assembly;

FIG. 3 is a cross sectional view illustrating the components of the syringe assembly in their assembled condition;

FIG. 4 is an enlarged cross sectional view illustrating two of the assembled components.

DESCRIPTION OF THE PREFERRED EMBODIMENT

Referring to FIG. 1, the main components of the unique hypodermic syringe assembly of the subject invention are illustrated in a position ready for assembly. A syringe barrel 10 has a flange 12 secured to its proximal end and a uniquely designed syringe tip 14 extending outwardly from its distal end. A conventional syringe plunger 16 having a thumb-contacting button 18 extends from the axial bore of syringe barrel 10 and is provided with a grommet 17 which is slidably positioned within the barrel to expel fluids therefrom when plunger 16 is moved in a distal direction.

The remaining components of the syringe assembly are a needle/hub assembly shown generally at 20 and a sheath 22 which, in the assembled condition, covers and protects the needle of the needle/hub assembly.

Referring to FIG. 2, syringe tip 14 is shown with an internal surface 24 which defines a passageway 26 that extends through the tip and communicates with an axial bore 28 extending through syringe barrel 10. Internal surface 24 is provided with a lead-in radius 30 which facilitates the assembly of the needle/hub assembly to the syringe tip in a manner to be hereinafter described.

Syringe tip 14 is also provided with an external surface 32 which is tapered inwardly from its proximal end to its distal end. Preferably, external surface 32 has a luer taper as hereinabove described. This conventional taper permits the syringe tip to be utilized with standard female luer tapered surfaces of conventional connectors if this mode of operation is desired.

The unique needle/hub assembly 20 of this invention will now be described in detail. Referring to FIG. 4, assembly 20 is illustrated in its assembled condition with hub 40 removably positioned in passageway 26 and occupying substantially the entire volume of the passageway. It will be appreciated that, because of manufacturing tolerances, it may be impossible to completely eliminate the dead air space within passageway 26, but this design essentially eliminates the necessity of purging air bubbles that are commonly present in conventional syringe assemblies. Hub 40 is provided with a central bore 42 and hollow needle 44 is secured within bore 42 in fluid communication with axial bore 28 in syringe barrel 10. Any suitable securement means may be utilized to secure needle 44 within bore 42, but it has been found to be very effective to provide a reservoir 46 and undercut areas 48 in the distal end of hub 40 into which a suitable epoxy adhesive may be injected to securely lock needle 44 within the hub bore.

A generally cylindrically-shaped skirt 50 extends outwardly and proximally of the distal end of hub 40. Skirt 50 serves to protect external surface 32 from contamination during handling and use so that the surface will be clean enough to use with a standard needle hub when needle/hub assembly 20 is removed from the syringe tip. It will be noted that skirt 50 is spaced radially outwardly from surface 32 and, therefore, does not interfere with the mounting and removal of needle/hub assembly 20 with respect to syringe tip 14.

Referring to FIG. 3, sheath 22 is illustrated in position overlying skirt 50. The function of the sheath is to cover needle 44 to prevent damage to the needle and injury to the customer and the sheath is also used to transmit an axial force to hub 40 during assembly of the hub onto syringe tip 14. To allow this axial force without permitting the sheath to be forced further onto skirt 50, the sheath is provided with a step 52 in its internal diameter. Step 52 is substantially perpendicular to the axis of the sheath and abuts the distal end of skirt 50 to prevent further axial movement. Since sheath 22 is designed to have an interference fit with the external surface of skirt 50, the sheath is securely but removably held onto the skirt. Also, if it is desired to remove needle/hub assembly 20 from syringe tip 14, the interference fit of the sheath to the skirt is used to transmit torque applied by the sheath to the skirt, thus enabling the user to twist the needle/hub assembly relative to syringe tip 14 until the fit of the assembly to the tip has been loosened. To increase the amount of torque which may be transmitted, the sheath and the skirt may be provided with matching axial ribs (not shown) or other suitable means. A set of splines 54 which form an interrupted flange around the proximal end of the sheath facilitate the handling of the sheath.

Although many materials are suitable for the various components of the hypodermic syringe assembly of the present invention, the preferred material for sheath 22, hub 40 and syringe barrel 10 is polypropylene. Alternate material for these components include all plastics with the requisite drug compatibility, including polyethylene, polystyrene, polyvinyl chloride, cellulose acetate and phenolics. In addition to the plastic materials mentioned above, hub 40 may be made entirely of brass, aluminum, steel or other suitable metallic materials.

In alternative embodiments, needle 44 may be secured to hub 40 by means other than epoxy. For example, if hub 40 is made of metal, the hub may include a tip protruding from the face region and this tip could be crimped about the needle to secure it within the hub bore.

In order to facilitate the mounting and removal of hub 40 within passageway 26, the components are preferably provided with matching tapers. For example, it is preferable that passageway 26 taper outwardly from its proximal to its distal end. It has been found that a passageway tapering from approximately 0.08 inch at its proximal end to approximately 0.095 inch at its distal end will provide a suitable taper which facilitates the mounting and removal of hub 40 within the syringe tip. It is contemplated that the unique hypodermic syringe assembly of this invention will be manufactured, assembled and supplied to the customer in a totally assembled condition as illustrated in FIG. 3. This will permit the customer to merely unpackage the assembly, remove sheath 22 and utilize the syringe for its intended purpose. The syringe, in this mode, provides a substantially air-free product which may be used without the necessity of purging air therefrom as is now necessary with conventional syringes. On the other hand, if it is desired to utilize the syringe barrel and tip with a conventional luer tapered needle hub, the user may remove needle/hub assembly 20 from syringe tip 14 by merely exerting a loosening torque and an axial force thereon and thereby exposing external surface 32 onto which the conventional hub may be mounted.

It will be apparent from the foregoing description that a unique dual-function hypodermic syringe assembly has been provided by the subject invention.

What is claimed is:

1. A hypodermic syringe assembly comprising:
 a syringe barrel having an axial bore therethrough;
 a tip integral with said barrel and having a passageway axially therethrough providing fluid communication with the axial bore of said barrel and the interior surface of said passageway having a converging taper from said tip toward said barrel; and,
 said tip having an external surface having a diverging taper from said tip to said barrel, said exterior surface adapted to conform to the female tapering surface of a conventional needle hub;
 a needle/hub assembly including:
 a hub with an exterior surface having a converging taper conforming to the converging taper of the interior surface of said passageway in said syringe tip, said hub removably positioned in said passageway and occupying substantially the entire volume of said passageway, and said hub being held in said passageway only by frictional engagement of the tapering internal surface of said passageway with the conformingly tapering confronting exterior surface of said hub;

said hub having an axial bore therethrough providing fluid communication with said syringe barrel in which axial bore a needle may be secured;

said needle hub assembly further including a radially extending portion extending from the distal end thereof; and, a generally annular skirt extending proximally from the radial periphery of said radially extending portion and disposed about said hub and having an interior surface confronting the exterior surface of said hub and tapering in conformity with the diverging taper on the exterior surface of said tip;

said skirt and said hub defining a space into which said tip depends when said hub is inserted into said tip passageway;

the confronting interior surface of said skirt and exterior surface of said tip being spaced apart to provide a clearance fit therebetween when said hub is frictionally positioned within said syringe tip passageway;

whereby the syringe assembly may be used with said hub positioned within said passageway to provide a substantially air-free syringe or said hub and needle may be removed from said tip to permit a conventional needle hub to be placed thereon.

2. The hypodermic syringe assembly according to claim 1 further including a protective sheath for said needle connected to the external surface of said skirt in an interference fit to transmit sufficient torque to said hub from said skirt through said radially extending portion when said sheath is twisted to thereby separate the sheath and said needle/hub assembly together from the tip of said syringe;

whereby the exterior surface of said needle tip is left undamaged by the application of said torque by reason of the spaced apart relationship between the external surface of said tip and the confronting interior surface of said skirt.

* * * * *